United States Patent
Melese et al.

(10) Patent No.: US 7,027,353 B2
(45) Date of Patent: Apr. 11, 2006

(54) METHOD AND APPARATUS FOR REAL-TIME VIBRATION IMAGING

(75) Inventors: Philip Melese, Palo Alto, CA (US); Robert A. Brown, Palo Alto, CA (US); Richard C. Honey, San Mateo, CA (US); Victor Aguero, Los Gatos, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 10/817,116

(22) Filed: Apr. 2, 2004

(65) Prior Publication Data

US 2004/0252587 A1 Dec. 16, 2004

Related U.S. Application Data

(60) Provisional application No. 60/460,542, filed on Apr. 3, 2003.

(51) Int. Cl.
*G01H 9/00* (2006.01)
(52) U.S. Cl. ............................................. 367/7; 73/657
(58) Field of Classification Search .................... 367/8, 367/7; 73/656, 657, 658, 603, 655
See application file for complete search history.

(56) References Cited

U.S. PATENT DOCUMENTS

| | | | | |
|---|---|---|---|---|
| 4,905,202 A | * | 2/1990 | Robillard | 367/8 |
| 5,005,419 A | * | 4/1991 | O'Donnell et al. | 73/626 |
| 6,134,006 A | * | 10/2000 | Telschow et al. | 356/503 |
| 6,792,811 B1 | * | 9/2004 | Argento et al. | 73/655 |
| 2002/0143245 A1 | * | 10/2002 | Rather et al. | 600/407 |

* cited by examiner

Primary Examiner—Ian J. Lobo
(74) Attorney, Agent, or Firm—Lumen Intellectual Property Services, Inc.

(57) ABSTRACT

A system and method for detecting vibration information by receiving electromagnetic radiation reflected or emitted from a target object at a photodetector array to provide real-time imaging of the target object. The detected radiation may be visible light, infrared or ultraviolet radiation, and/or of other desired frequency ranges. The detected radiation is AC-coupled to isolate components relating to oscillations of the target object from components relating to ambient radiation, e.g. background sunlight, and is digitized, stored, and subjected to processing such as a Fourier transform to generate outputs representative of frequencies of oscillation, which can be used for analysis of the target object.

47 Claims, 18 Drawing Sheets

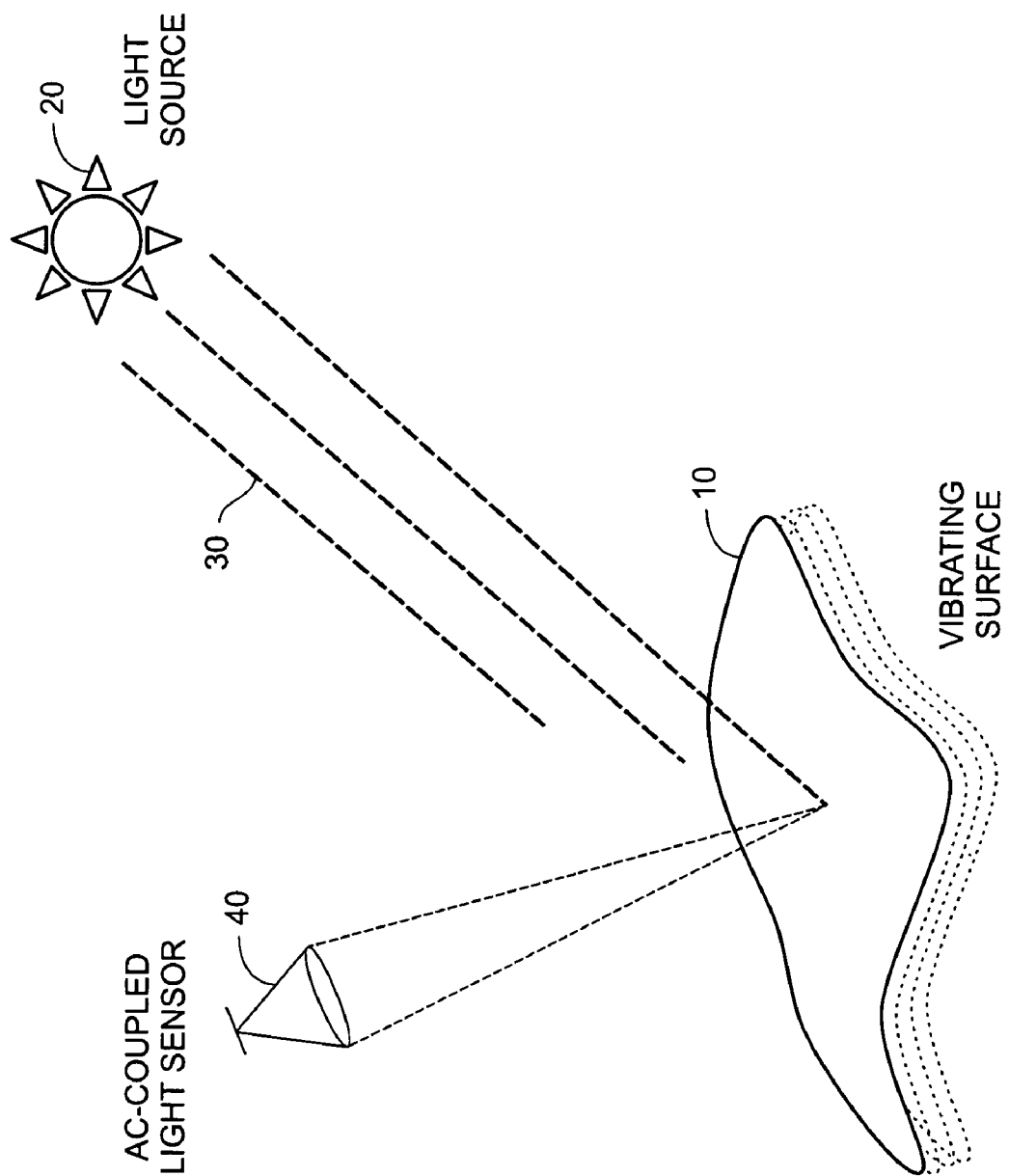
FIG._1

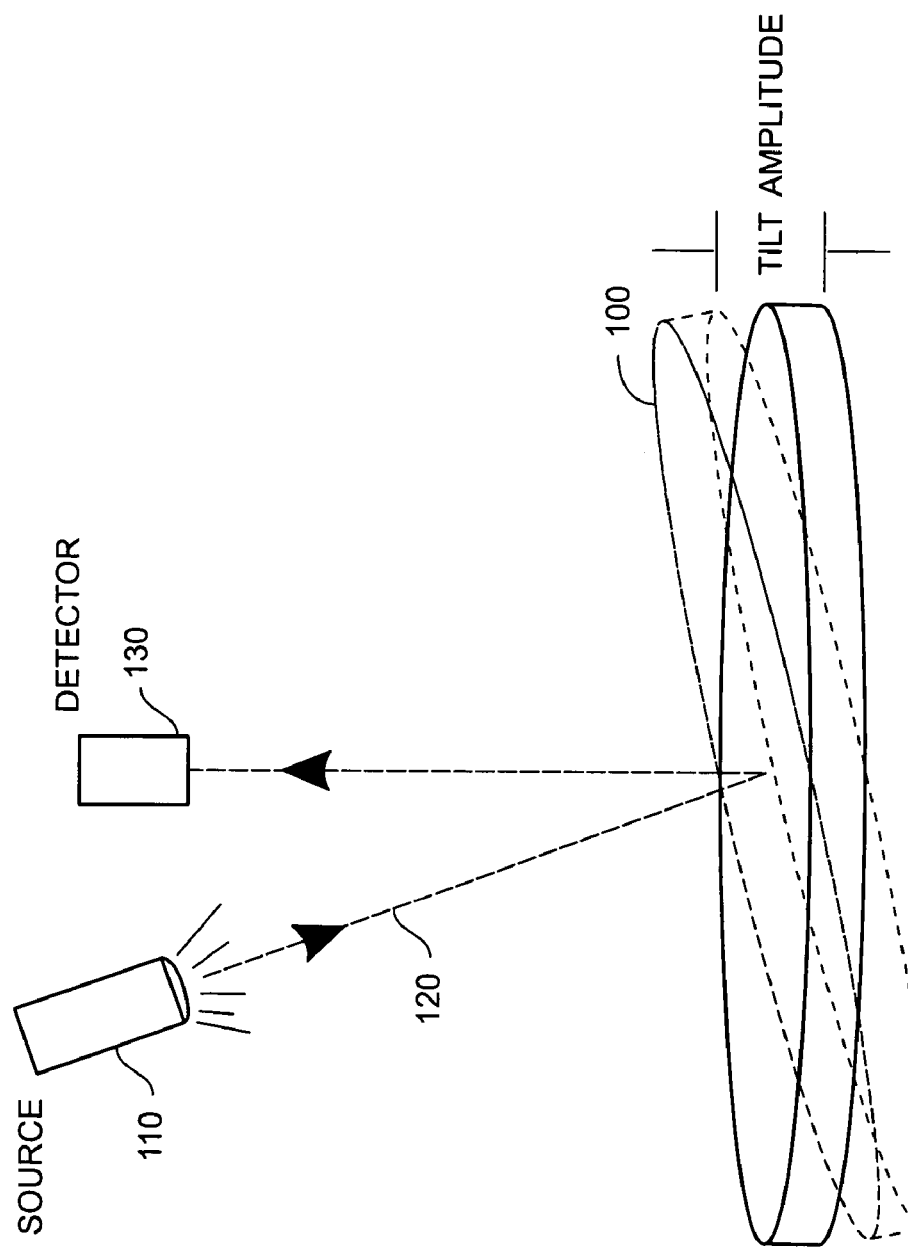
FIG._2

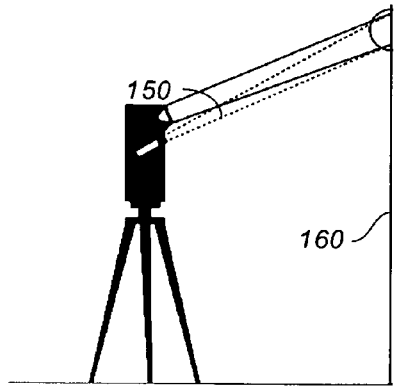
FIG._3A
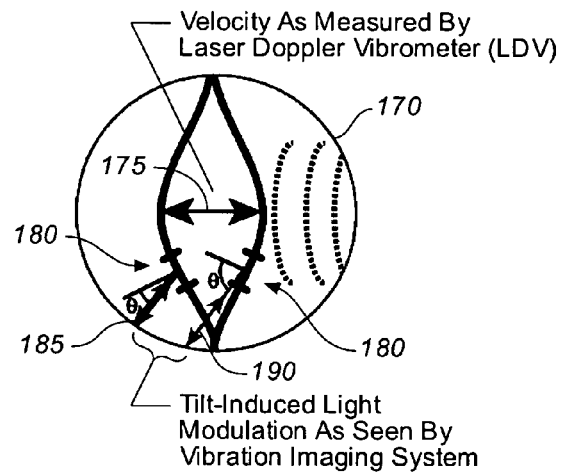
FIG._3B
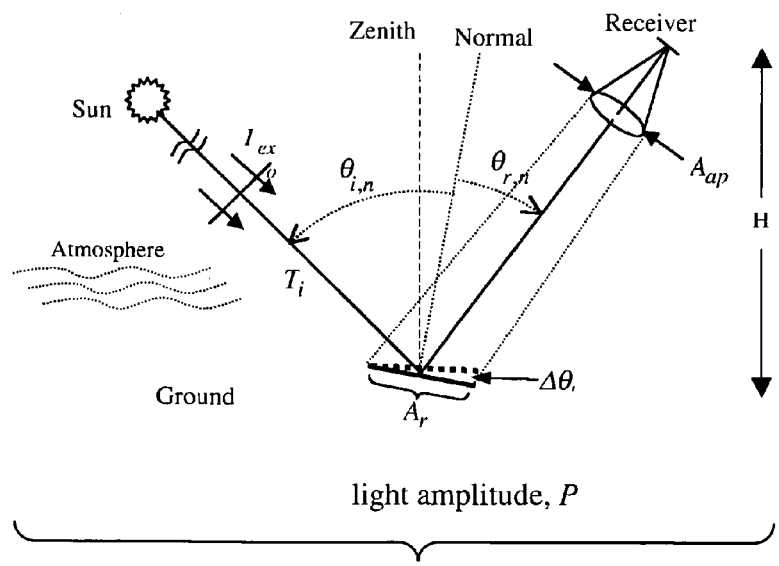
FIG._4

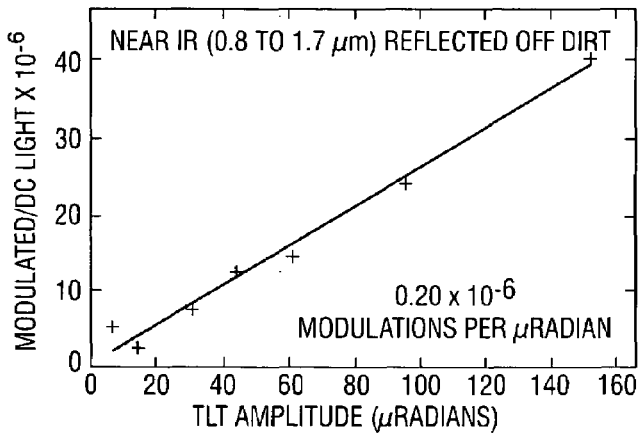
FIG._5
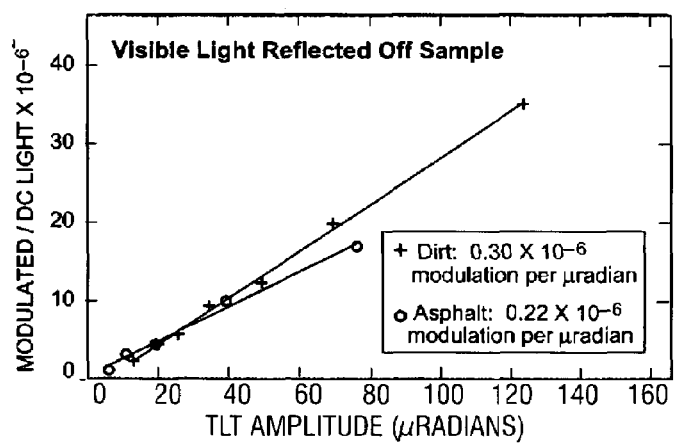
FIG._6
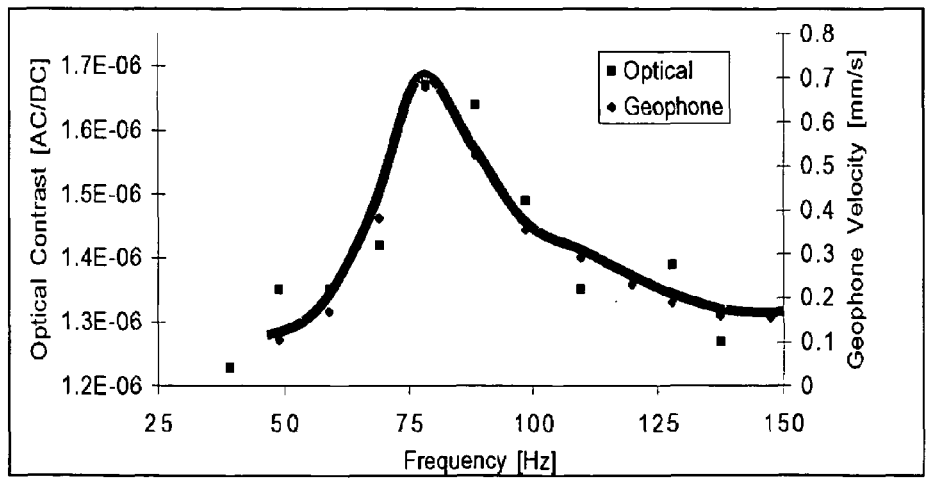
FIG._7

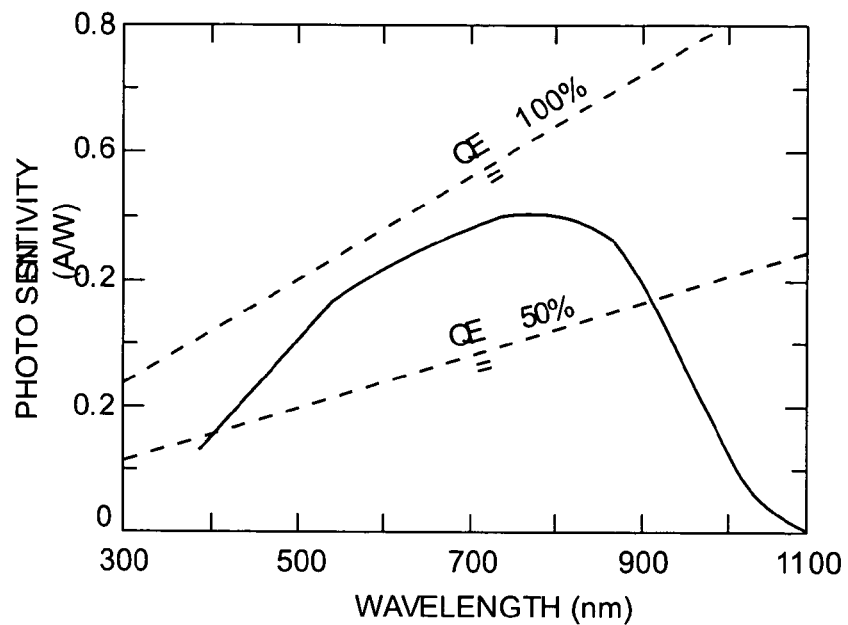
FIG._8
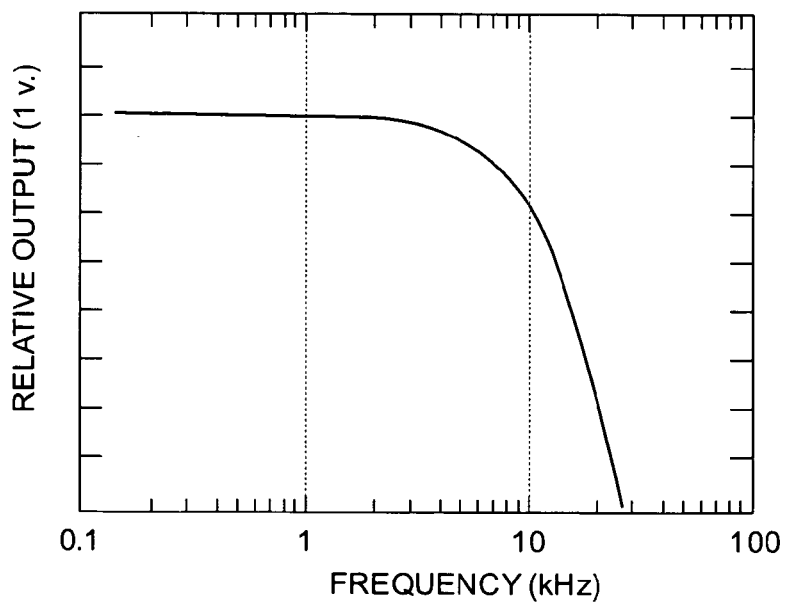
FIG._9

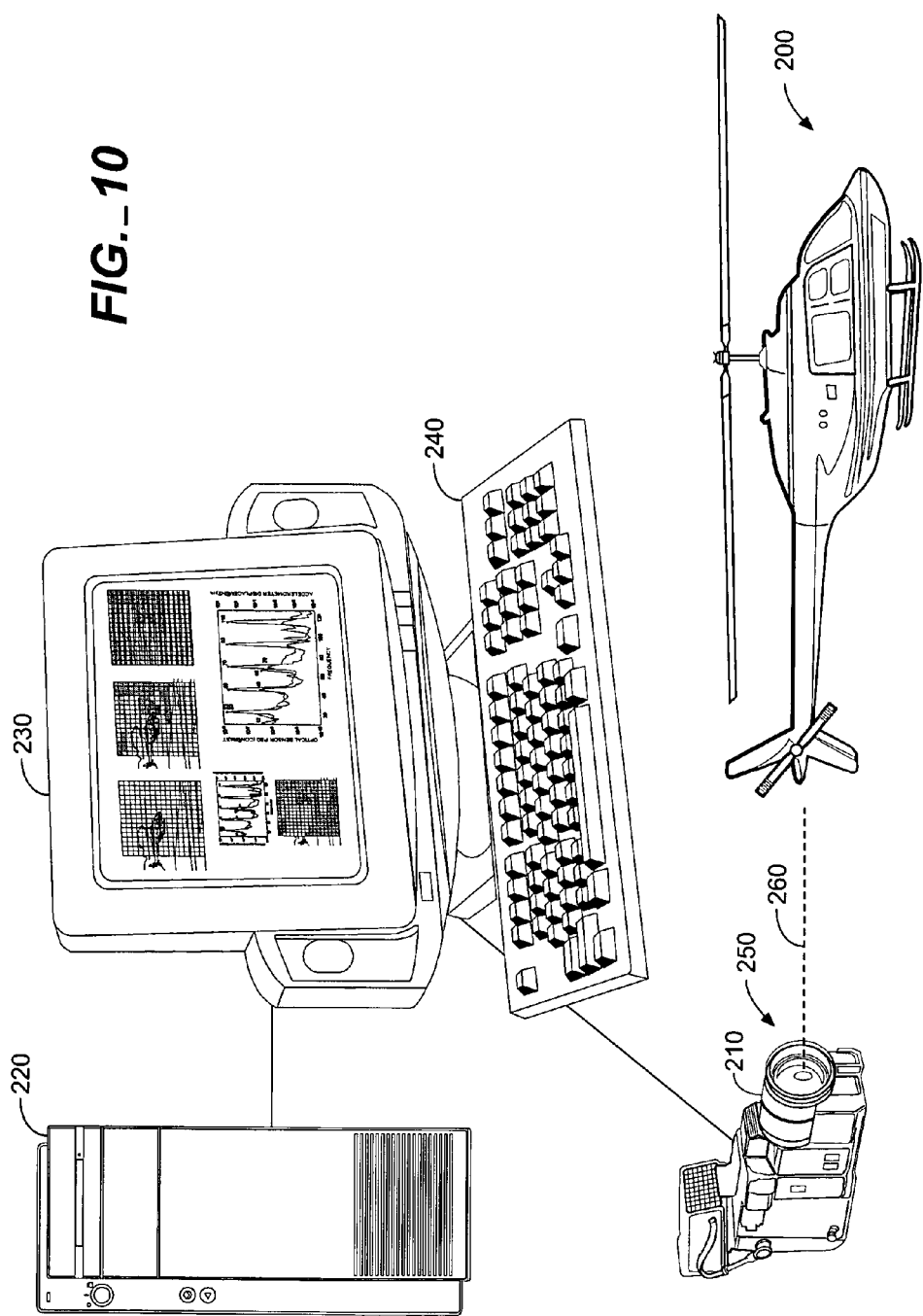

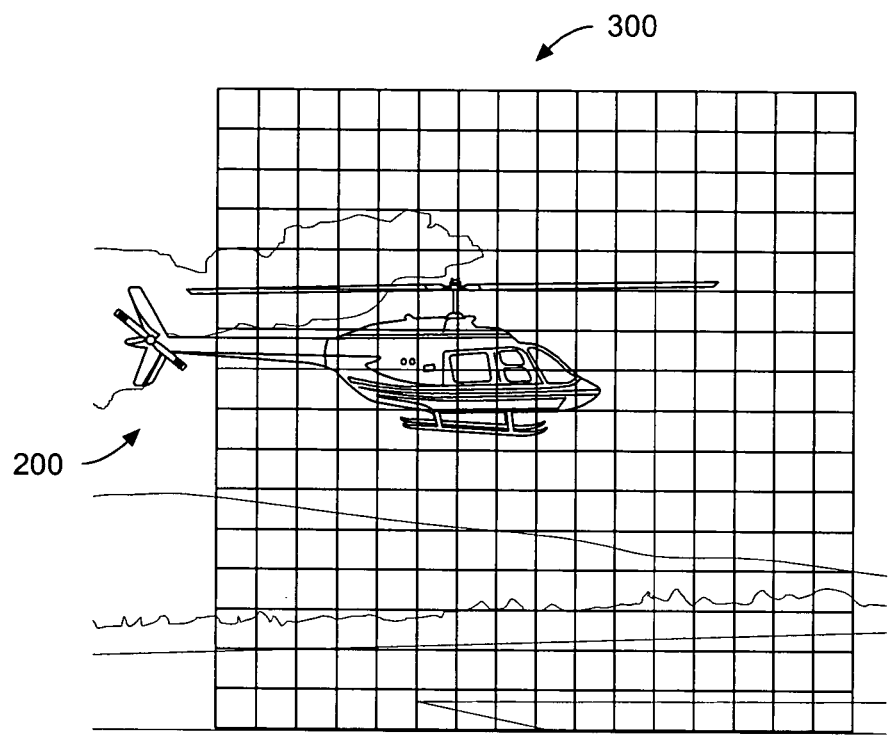
FIG._11
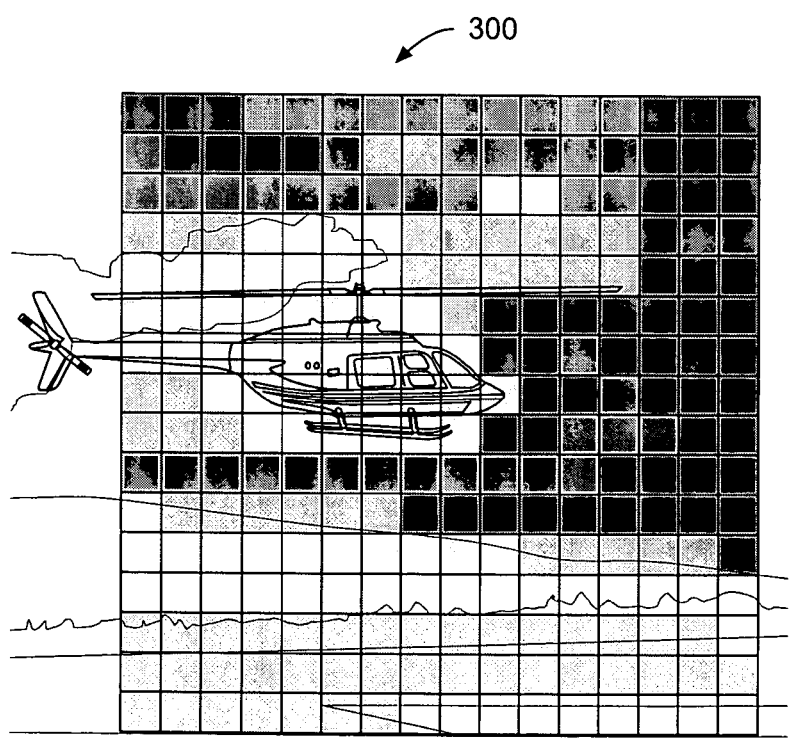
FIG._12

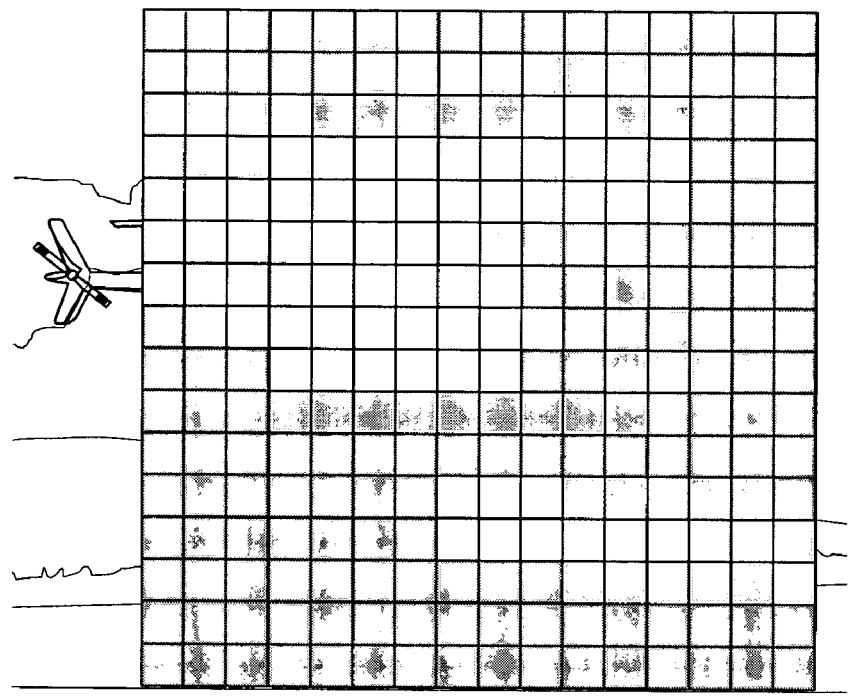
FIG._13
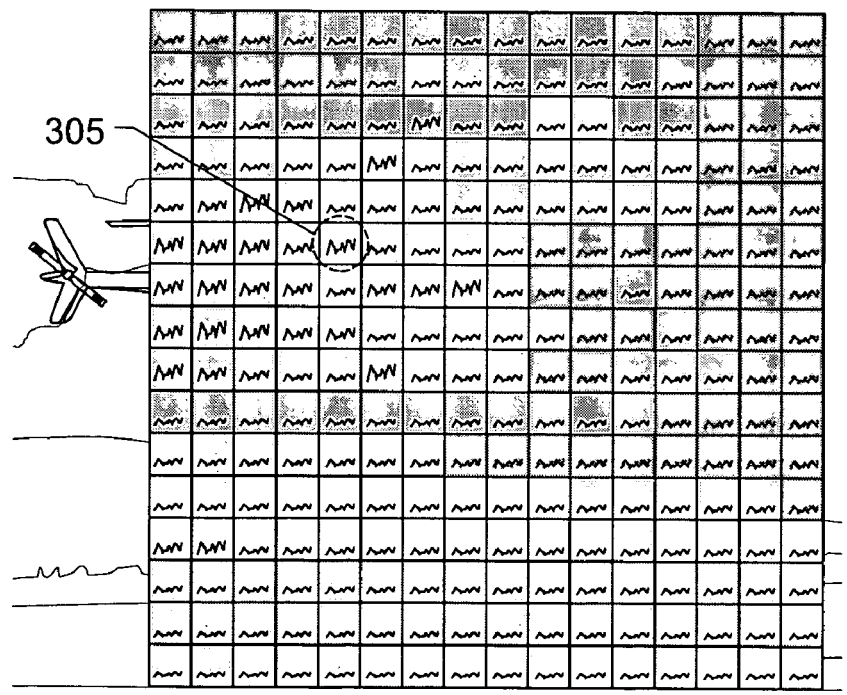
FIG._14

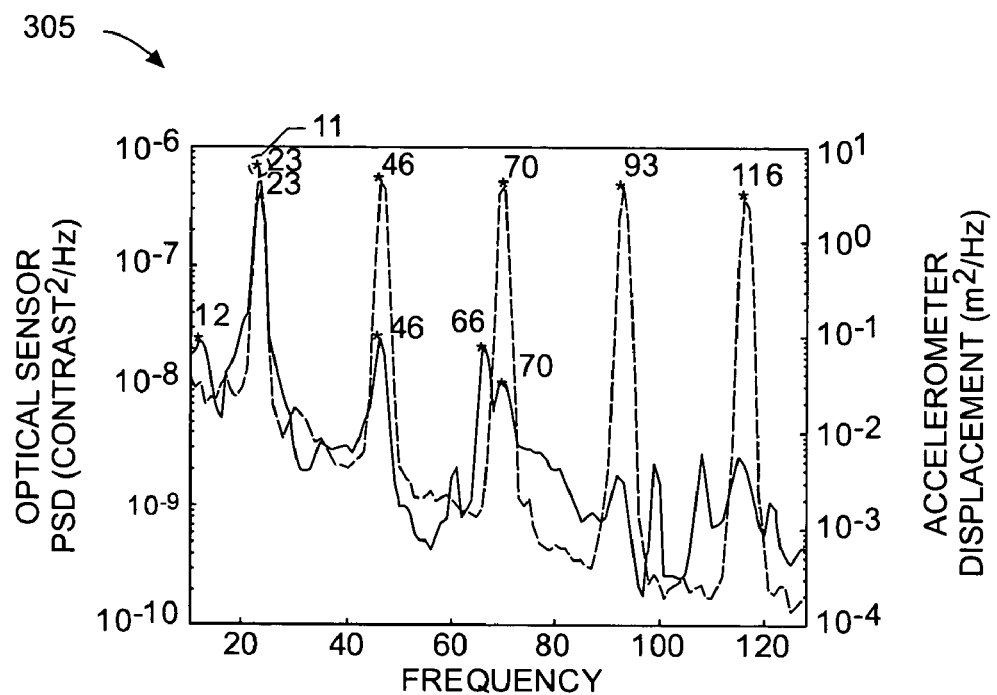
FIG._15
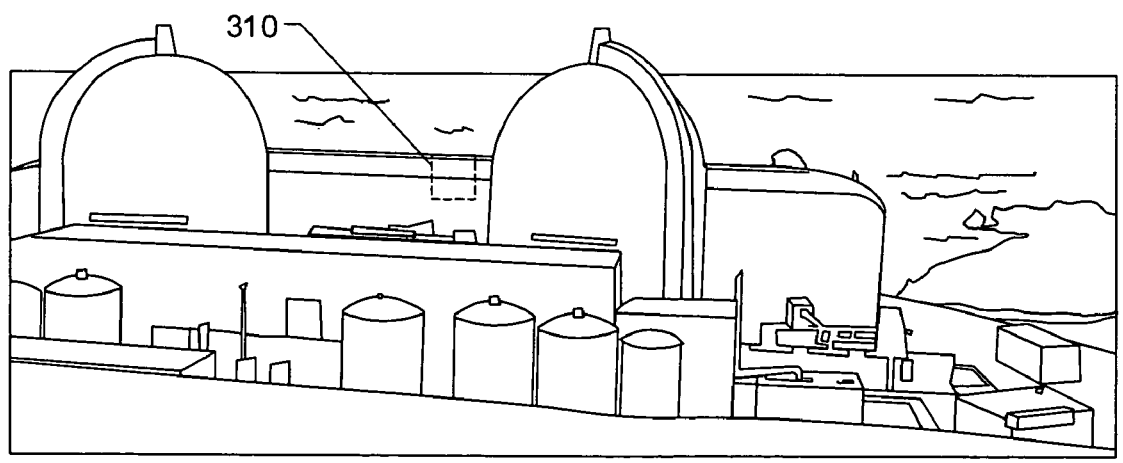
FIG._16

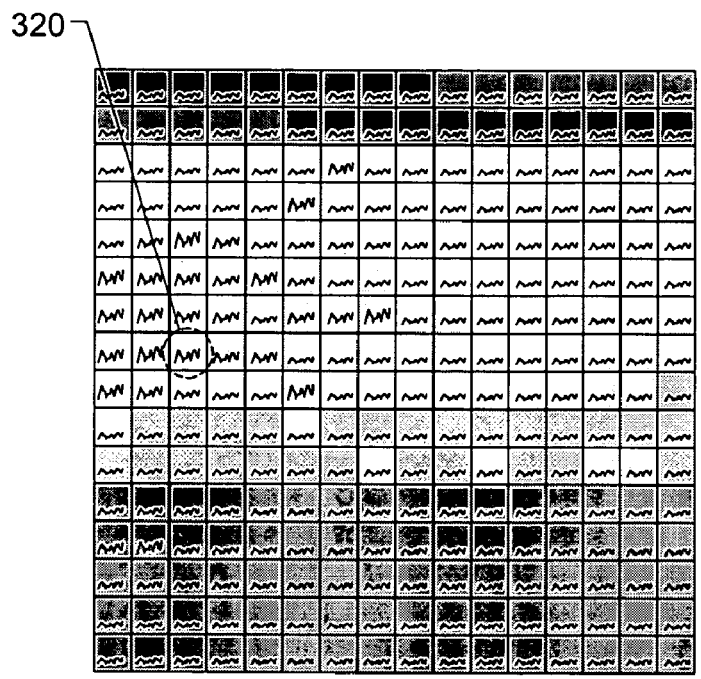
FIG._17
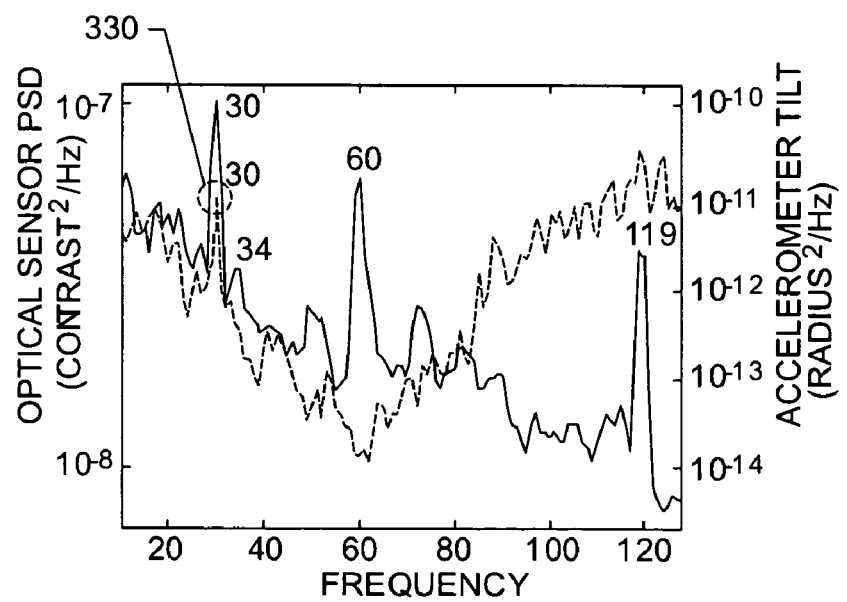
FIG._18

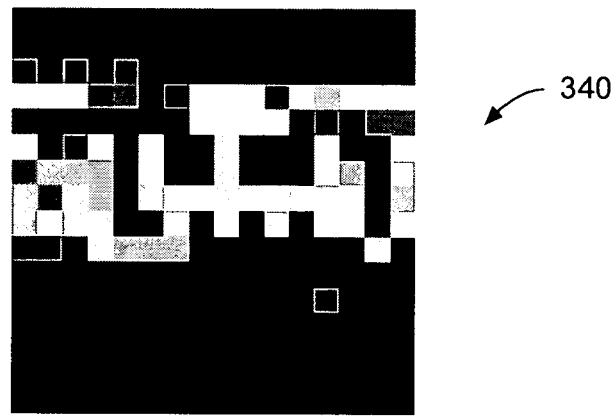
FIG._19
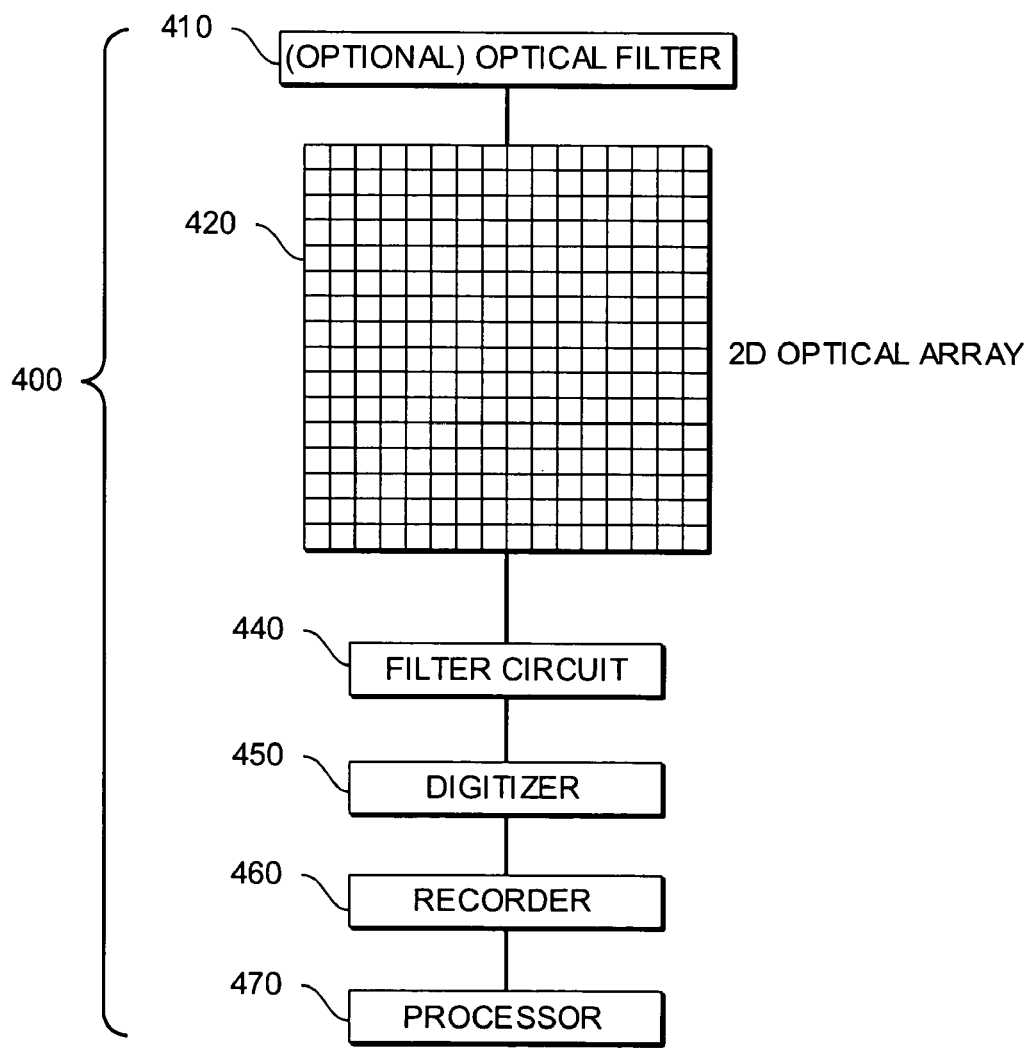
FIG._20

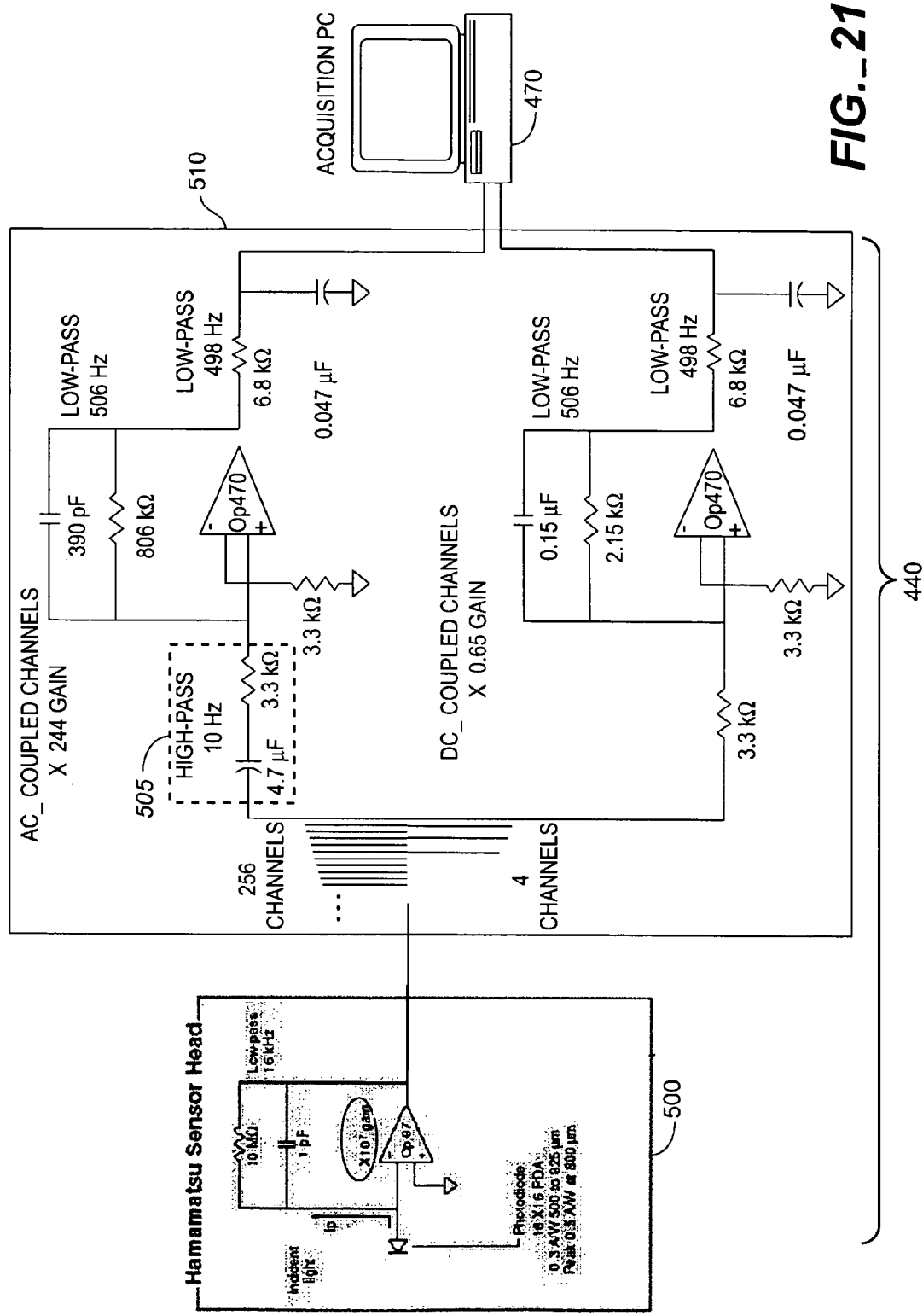
FIG._21

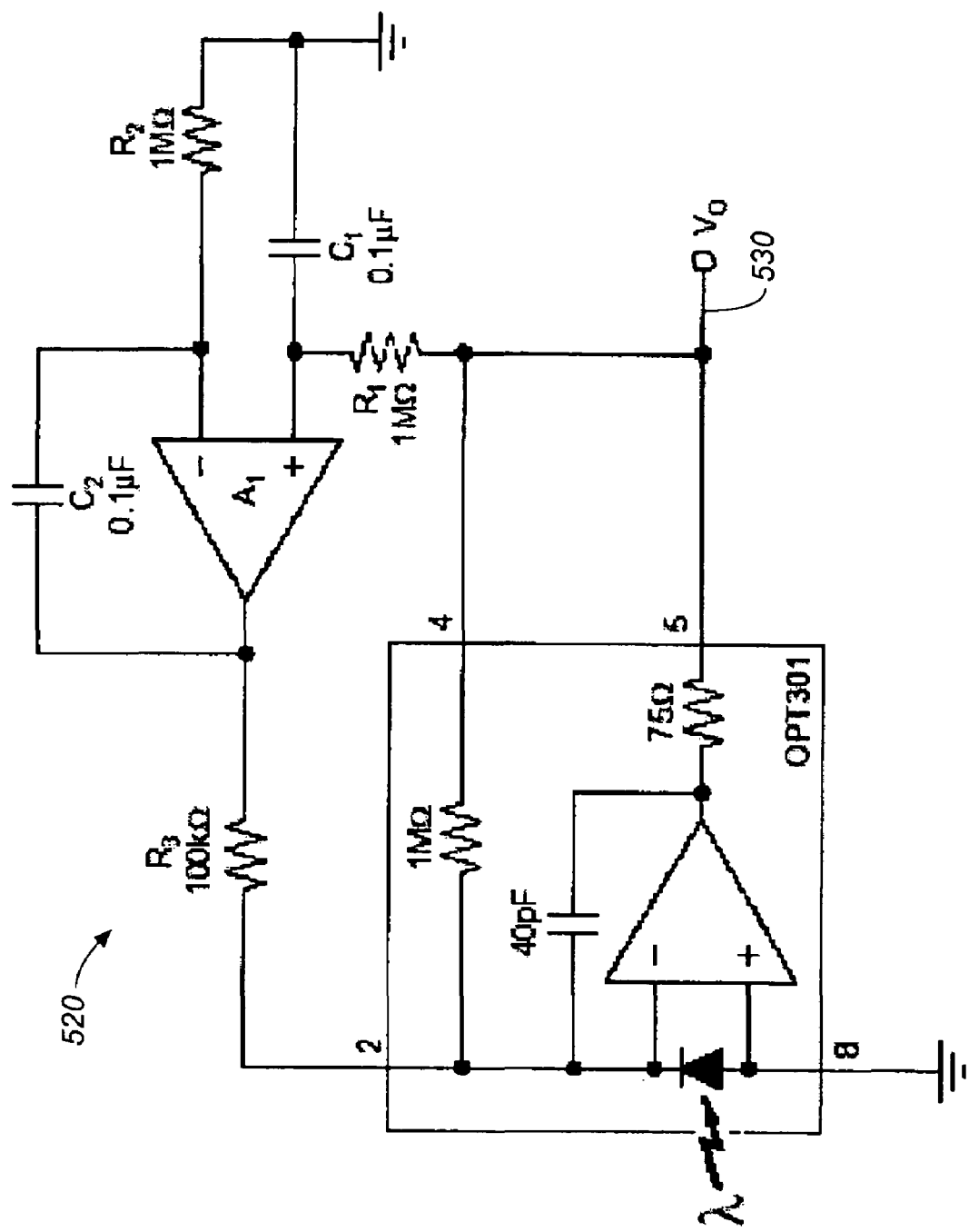
FIG._22

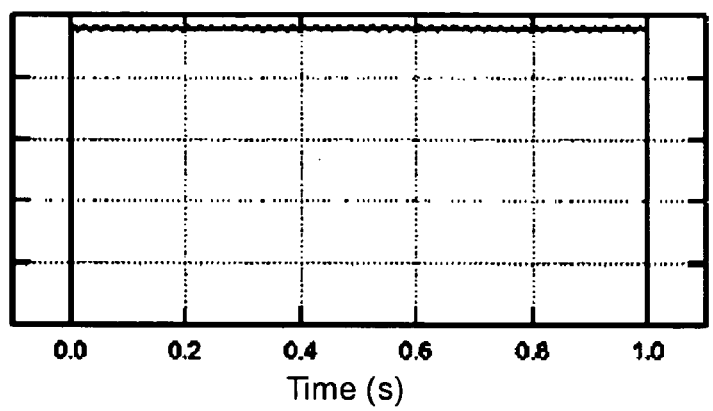
FIG._23A
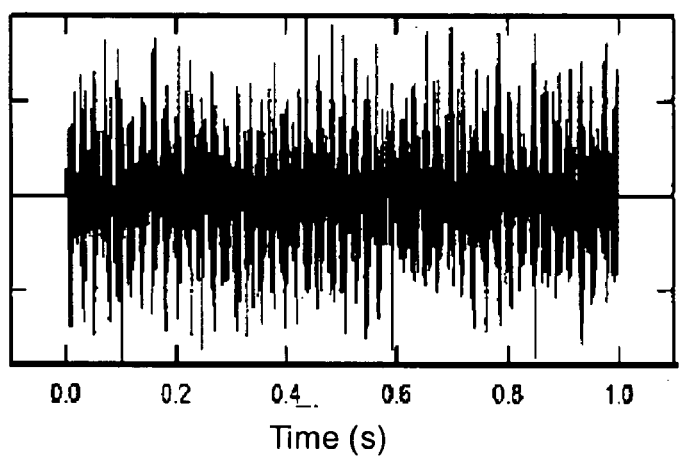
FIG._23B
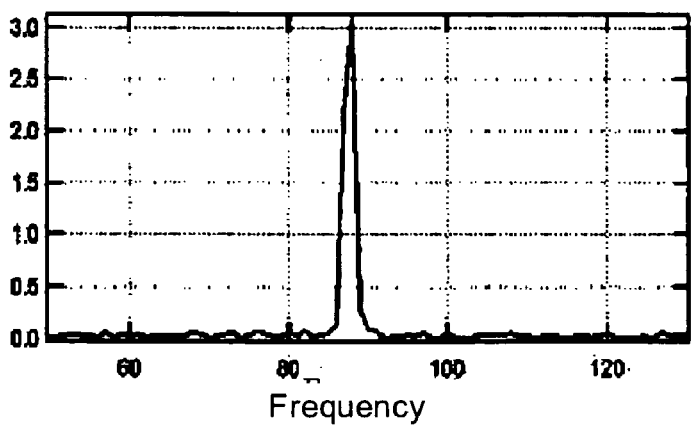
FIG._23C

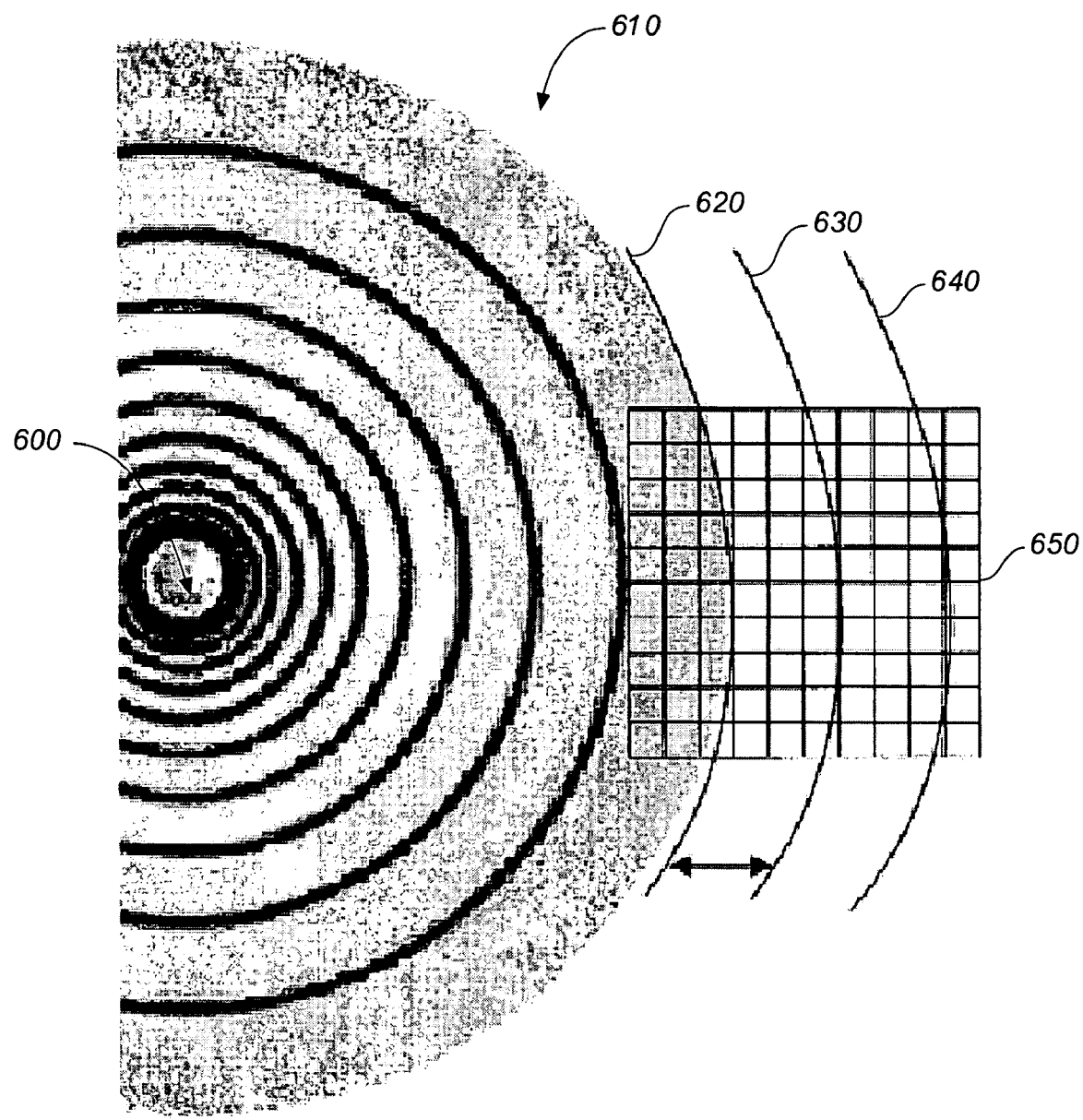
FIG._24

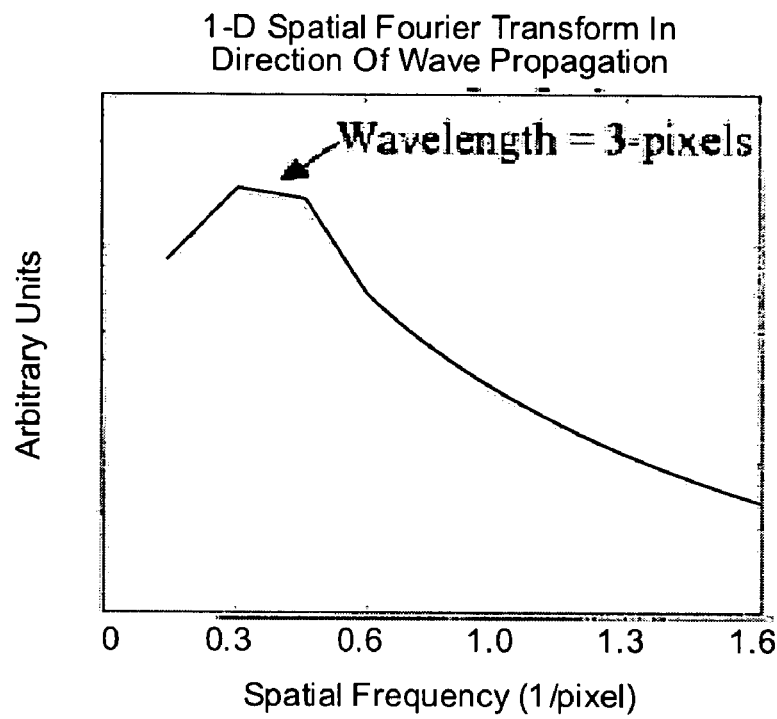
FIG._25
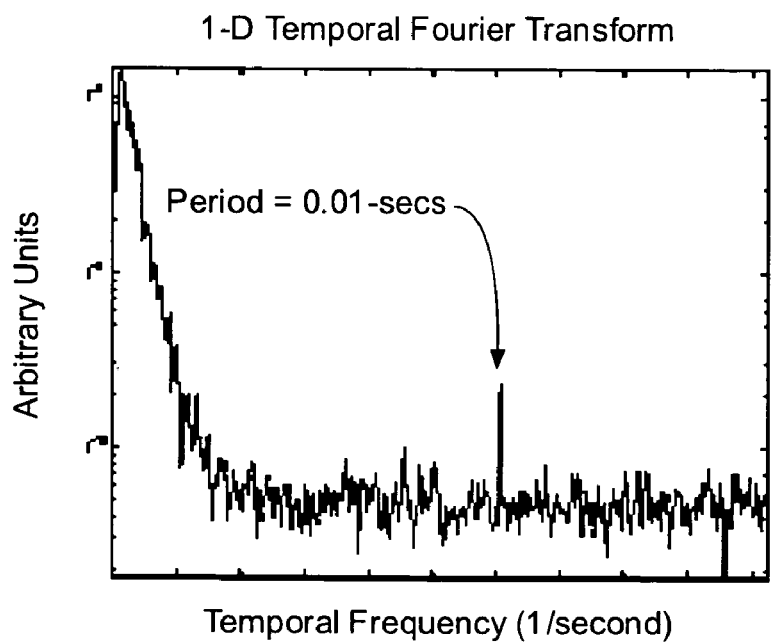
FIG._26

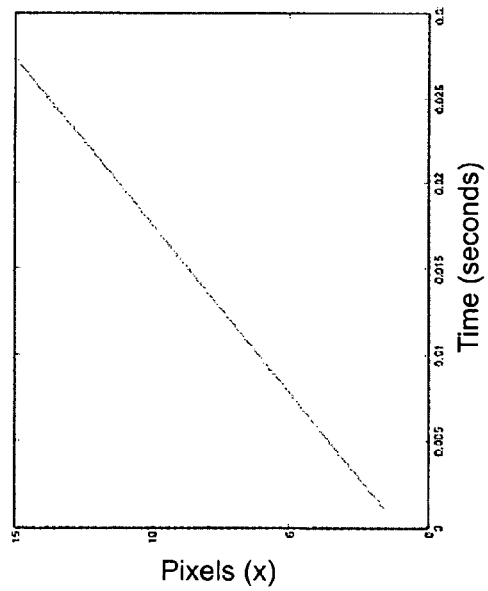
*FIG._28*
Space-Time Distribution
(3-D provides Direction Vector in X-Y Plane)
Pixels (x) vs Time (seconds)
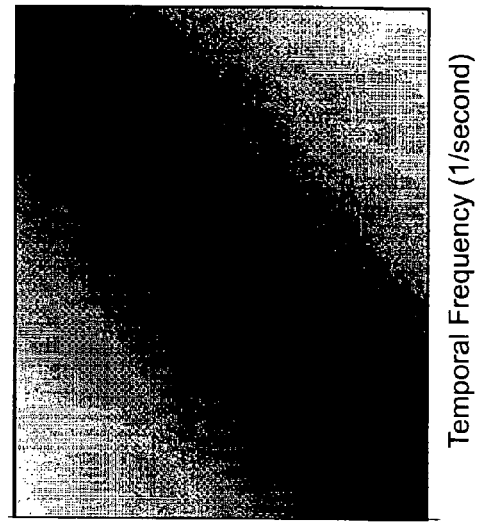
*FIG._29*
2-D Spatial-Temporal Fourier Transform
(3-D Provides Direction Vector In X-Y Plane)
Spatial Frequency (1/second) vs Temporal Frequency (1/second)
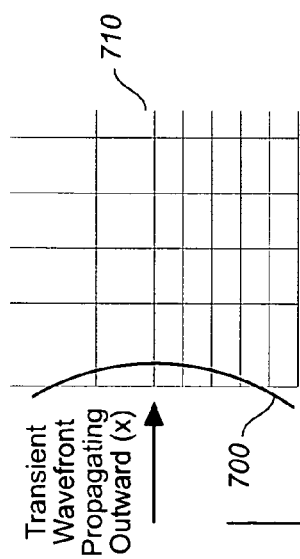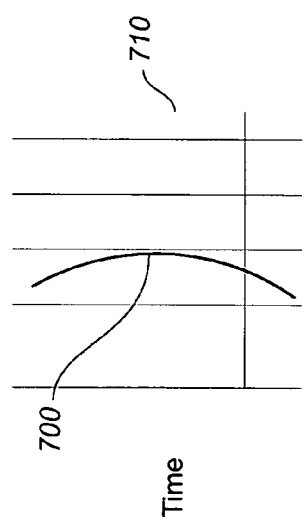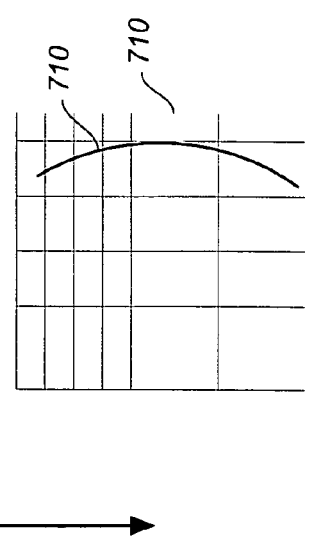
*FIG._27*
Transient Wavefront Propagating Outward (x) — Time

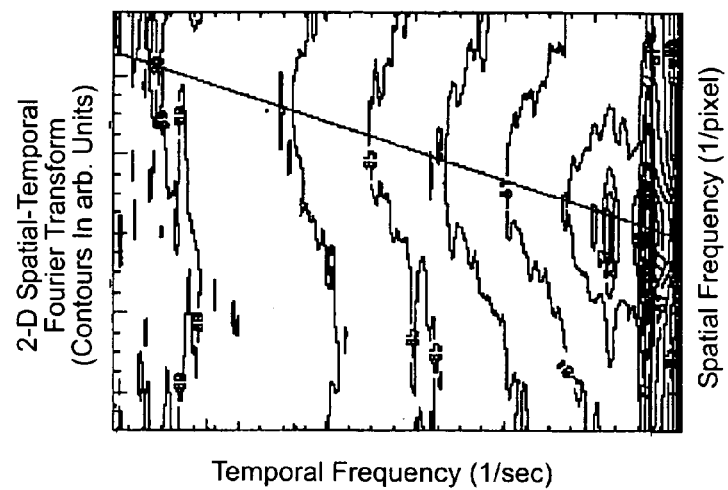
FIG._31
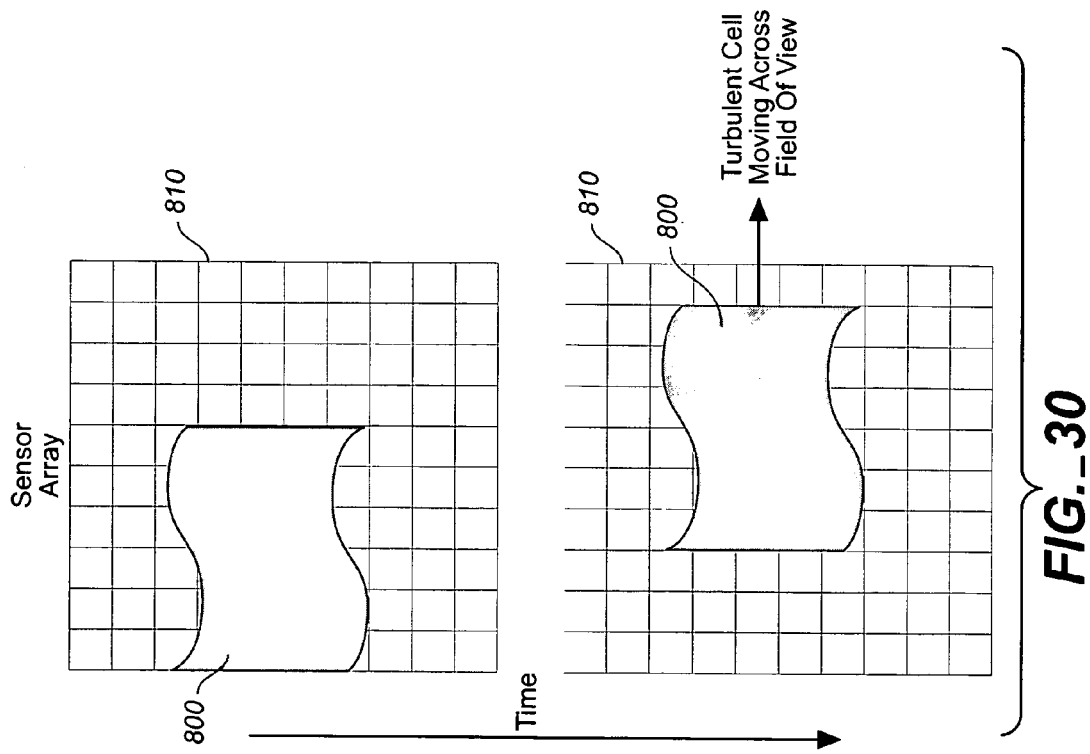
FIG._30

METHOD AND APPARATUS FOR REAL-TIME VIBRATION IMAGING

This application claims the benefit of U.S. Provisional Patent Application No. 60/460,542 filed Apr. 3, 2003 and entitled "System and Method to Remotely Detect, Image, and Characterize Ground Vibration or Vibrating Objects or Surfaces" by Melese, et al., and incorporates that application by reference.

The invention was made with Government support under contract number 98-C-3218 awarded by the Government. The Government has certain rights in this invention.

BACKGROUND OF THE INVENTION

The present invention relates to a system and method for remotely detecting objects that undergo vibration or other acoustic or seismic stimulation, including single-pulse shocks.

Various systems have been used to detect vibrations in target scenes or objects, including seismic detectors, using such apparatus and techniques as accelerometers, laser Doppler vibrometry or velocimetry (LDV), near-field acoustic holography, and so on. In the cases of accelerometers and LDV, apparatus currently in use detects oscillations at single points or regions of interest, with high precision but lacking the ability to generate an acoustic signal image of the target region and thus lacking the ability to derive useful information from such an image. For instance, certain phenomena, such as transient acoustic signals and turbulent events, cannot readily be detected in the signal analysis of acoustic signals from a target region with the use of single-point detectors.

Near-field acoustic holography can detect acoustic signals from multiple points, based upon sound pressure, but the complexity of the necessary equipment and set-up is high, and thus does not present a practical approach for many applications.

A system is accordingly needed that can simultaneously and in real time detect, sample and process acoustic signals (which may be seismic signals, as discussed below) from multiple correlated points on a surface of a target region of interest, to generate displays and otherwise output analytical information relating to the entire target region, with equipment that is quickly and easily set up, without requiring contact or proximity with the target region.

SUMMARY OF THE INVENTION

A system according to the invention includes a photodetector array that is configured to receive light reflected or emitted from a target object (or scene). The light from the target object modulates due to vibrations in the target object. The received light is sampled at some predetermined frequency, such as at 1 kHz, and is periodically stored, such as once per second, to generate a series of data. Each set of periodically stored data thus includes time-correlated signals received at the photodetector array, and each photodetector of the array receives light from a particular region of the target object, so that a series of full images of the target object is generated, each image including oscillation data for the regions of the target object derived from the modulated light, which may accordingly be referred to as acoustic or acoustically derived signals.

The received signals are AC-coupled (high-pass filtered) to isolate oscillation information from information relating to ambient light reflected from the target object. The filtered acoustic signals are subject to analysis or transformation, such as a Fourier transform, to extract frequency information from the signals.

This frequency information can be used for various types of analysis. If the target object is a building that houses machinery, the frequency information can be used to monitor vibrations for any changes that might indicate a problem with the machinery. If the target object is a region of the earth's surface, the system may be used in conjunction with seismic exploration techniques to detect subsurface structures such as oil deposits, aquifers, mineral veins, or the like, or to detect buried artificial objects such as pipelines, power lines, and so on.

The received light may be optically filtered at the detector array to remove unwanted components of ambient radiation.

The system and method of the invention provide the capability of analysis of the acoustic signals to identify both oscillatory phenomena and transient events, as well as to detect turbulent events in the target scene.

BRIEF DESCRIPTION OF THE DRAWINGS

FIG. 1 is an illustration of light reflecting from a vibrating surface to a light sensor.

FIG. 2 is an illustration showing tilt amplitude in a vibrating surface similar to FIG. 1.

FIGS. 3A–3B illustrate a basic configuration of apparatus according to the invention.

FIG. 4 shows a more detailed geometry of a setup of apparatus according to the invention.

FIG. 5 is a graph of infrared light reflected from a sample (dirt).

FIG. 6 is a graph of visible light reflected from samples (dirt and asphalt).

FIG. 7 is a graph comparing results of an apparatus according to the present invention with a conventional geophone used for seismic-acoustic detection.

FIG. 8 is a graph illustrating a spectral response of an apparatus according to the invention as used in a biological application.

FIG. 9 is a graph illustrating frequency response of an apparatus according to the invention in the setting of FIG. 8.

FIG. 10 is an illustration of one embodiment of apparatus according to the invention.

FIGS. 11–14 illustrate superimposition of detected array data generated according to the invention over a target region of interest.

FIG. 15 is a graph illustrating comparative results of a system according to the invention using an optical sensor vis-á-vis results from an accelerometer.

FIG. 16 illustrates another target region of interest for vibration detection according to the invention.

FIG. 17 illustrates the correlation of spectral data with pixels in a detector array as used in the present invention, relating to the target region of FIG. 16.

FIG. 18 is a graph similar to that of FIG. 15, but relating to the target region of FIG. 16.

FIG. 19 is an illustration of a power distribution over a detector array in a system according to the invention for a particular frequency (here, 30 Hz), correlated with the target region of FIG. 16.

FIG. 20 is a block diagram of a system according to the invention.

FIGS. 21–22 are schematic diagrams of electronic filters and AC- and DC-coupling channels suitable for use in an apparatus according to the invention.

FIGS. 23A–23C illustrate isolation and removal of DC signals relating to ambient light from AC oscillation signals of interest in analyzing a target region according to the invention.

FIGS. 24–26 illustrate detection according to the invention of wavefronts propagating from a vibrating source.

FIGS. 27–29 illustrate detection according to the invention of a transient wavefront.

FIGS. 30–31 illustrate detection according to the invention of a turbulent cell across a target region.

DETAILED DESCRIPTION

A simple example of a vibrating surface 10 is shown in FIG. 1, wherein light source 20 emits electromagnetic radiation 30, which reflects from the surface 10 and at least in part is detected at a light sensor 40. The light source 20 may in general refer to any suitable source of electromagnetic radiation, and the radiation 30 may be of any of a number of ranges of wavelengths, e.g. visible light, infrared (IR), ultraviolet, etc. Thus, when the term "light" or "optical" is used herein, it will be understood that any desired frequency or range of frequencies of electromagnetic radiation may be used, and the light source may be naturally occurring (e.g. the sun) or artificial (e.g. a laser or a lamp). The sensor 40 is accordingly configured to detect the wavelengths of interest, and as discussed below includes circuitry and software as needed to capture, process, analyze and display frequencies, relative magnitudes and phase information of the detected light substantially simultaneously.

Although the present invention will be described in terms of light that is reflected from a scene, object, etc., it is equally applicable to detection of light that is emitted (e.g. due to fluorescence or thermal IR emission), and thus when reflection is mentioned it may be taken also to refer to emission, fluorescence, etc. In addition, reference to a detected "signal" should be taken to refer to any such radiation.

The term "acoustic" will be used herein to the broad sense of any acoustic, vibratory, pulsed, transient, turbulent or oscillatory phenomenon, as well as to events that are seismic, seismic-acoustic, hydroacoustic, etc., in character. Thus, the term "acoustic signal" as used herein may be taken to refer to acoustically derived representations of movements or vibrations of an object or surface, and in particular embodiments described herein include electromagnetic radiation of any suitable wavelength that is reflected, emitted, etc. from an object undergoing motion as detected by an apparatus according to the invention.

In general, the term "logic" as used herein refers to electronic circuitry, processor-based systems or subsystems or other hardware, software and/or firmware as appropriate to implement the teachings of the present invention, and where any one of these (e.g. a circuit or a processing program or routine) is referred to, it should be understood that other hardware, software or firmware may be used to equivalently implement the same functions or features.

Surfaces that are subject to shocks, oscillations or forces that otherwise cause them to move may set up characteristic vibrations, and in particular may vibrate at frequencies that are useful for analysis, e.g. to determine underlying faults or other causes in a target object or scene. As discussed below, the present invention is applicable to imaging and processing of signals detected from regular oscillations or from single-impulse or other nonrepetitive motions of a surface or a scene. Thus, where any of vibrations, oscillations, pulses or other motions are referred to herein, it will be understood that any combination of such motions (or lack of motion, for particular regions of a scene) may be present.

When the term "image" or "imaging" is used herein, it may refer either to logical representation of signals that can be correlated to corresponding regions of the target scene, and/or it may refer to an actual visual, display or printed representation of the signals, with or without a correlation with a representation of corresponding regions of the target scene.

Theoretical Concepts of the Invention

Vibration imaging (detection, processing and analysis) according to the invention utilizes the known phenomenon in optics that characteristics of light as reflected from a surface depend upon the angles of incidence and reflection of the light (i.e. incoming and outgoing angles) relative to the surface. The angular dependence of reflectance from a surface is called the bidirectional reflectivity distribution function (BRDF). An additional signal contribution comes from the purely geometrical tilt-induced change in flux of the incident collimated light on an imaged surface. In real-life complex scenes, sharp transitions in reflectance and shadows can amplify the induced contrast in the acoustic signal.

Vibratory motions modulate this surface tilt, in turn modulating the angles and thus the reflectance. The net result is that the vibratory motion modulates the amplitude of light reflected from the surface. Vibration imaging according to the present invention detects the modulation of light reflected from many small areas on the surface simultaneously, and is therefore a measure of surface motion (or lack of motion, for regions undergoing no vibration) in terms of tilt. The optical "contrast," defined in one embodiment as the tilt-induced change in light amplitude (light modulation) divided by the total light amplitude (the ambient or DC light), is substantially proportional to the surface tilt for small angle changes. Other definitions of "contrast" as used herein may be suitable, with the common concept being that the tilt-induced change in light amplitude is detected and used to determine the vibration characteristics as described.

FIG. 2 illustrates a vibrating (or otherwise moving) surface 100, and light source 110 transmits light 120 to the surface 100. The light 120 reflects from the surface to detector 130, and is modulated depending upon the tilt amplitude of the surface 100.

FIGS. 3A–3B illustrate in greater detail a basic configuration of the invention, showing a detection apparatus 150 aimed at a surface 160, with enlargement 170 detailing a local perturbation of the surface. The tangential vector 175 represents the motion a laser Doppler vibrometer (LDV) (velocity) or an accelerometer would measure. The change in tilt of the small line segment 180 of the surface 160 denotes the field of view of a single pixel, which causes the light reflection angle ($\theta$) to change from that shown as arrow 185 to that shown as arrow 190 and then back again as the surface vibrates. The change in reflectivity with this angle is described in greater detail below. The modulation in the light intensity from a given "unit" area 180 as in FIG. 3B is measured by one of the pixels in the image produced by a vibration imager of the invention. This "unit" area 180 may vary in size with different lenses or fields of view of a system according to the invention.

FIG. 4 shows a general deployment geometry for an imager that may be configured to incorporate features of the invention. A light source (which may be collimated, such as sunlight) impinges on the ground at an incident (subscript "i") angle of $\theta_{i,n}$, where subscript "n" indicates the angle with respect to the surface normal. The angle $\theta_{i,n}$ changes with ground motion. Similarly, the reflected light is viewed by the receiver (subscript "r") at an angle $\theta_{r,n}$ with respect to the normal.

The light source may as indicated be collimated, and/or it may be coherent (such as laser radiation), or it may be neither. For interior applications, an active collimated illuminator can be used, which has the advantage that it provides control over the light angles. The illuminator light can be broadband and visible, like sunlight, or it can be narrow-band (such as a near-IR laser). Photodiodes or other photodetectors of suitable sensitivity should be selected, depending upon the light source.

The light source should also be of sufficient intensity to limit shot noise and overcome background ambient light, and preferably have minimal temporal modulation, i.e. variation in the intensity of the light source over time. Battery-powered spotlights are suitable for many applications.

In prior systems, the use of an accelerometer or LDV entails measuring a single spot on the target surface at a time, so in order to spatially sample a surface (i.e. produce a vibration image), the LDV must be scanned or an array of accelerometers would have to be used. In the present system, by way of contrast, an array of simultaneous images is generated from, e.g., 256 contiguous (or alternatively, at least partly contiguous and possibly partly separated in space) target spots, thus providing a full-scene imaging sensor for analysis of the target scene.

Equation A-1 below gives the light amplitude P at the receiver in terms of the incident irradiance I, atmospheric transmission T, the BRDF b, an imaged surface element area $A_r$, the receiver aperture $A_{ap}$, the receiver height above the ground H, and the angular dependences. (Atmospheric transmission effects $T_i$ can be ignored for these short ranges.)

$$P = \qquad \qquad \qquad \qquad \text{(A-1)}$$

$$I_{exo} \cdot (T_{atm,0})^{\sec \theta_{i,z}} \cdot \cos \theta_{i,n} \cdot b(\theta_{i,n}, \theta_{r,n}) \cdot \frac{A_r \cos \theta_{r,n} A_{ap}}{(H/\cos \theta_{r,z})^2} \cdot (T_{H,0})^{\sec \theta_{r,z}}$$

Equation A-2 shows how the Vibration Imaging signal, the optical contrast $\Delta P/\langle P \rangle$ is proportional to the surface tilt $\Delta \theta_t$, i.e., the change in angle of the subtended area $A_r$ as the imaged surface vibrates. The proportionality has a geometrical dependence $\tan \theta_{i,n}$ on the incident light angle and terms arising from the partial derivatives of the BRDF b with respect to the incident and reflected light angles.

$$\frac{\Delta P}{\langle P \rangle} = \left[ \tan \theta_{i,n} - \frac{1}{b(\theta_{i,n}, \theta_{r,n})} \cdot \left( \frac{\partial b}{\partial \theta_{i,n}} + \frac{\partial b}{\partial \theta_{r,n}} \right) \right] \cdot \Delta \theta_t \qquad \text{(A-2)}$$

In the laboratory, data were collected using a controlled tilt-platform and various illumination and sensor angles, as shown in FIG. 2. The resulting plots of FIGS. 5 and 6 shows the substantially linear relationship between the measured optical contrast and the measured (using two displacement sensors) surface tilt for dirt and asphalt surfaces at different illumination wavelengths. This setup was used to verify that equation A-2 accurately describes the dependence of the optical contrast on the illumination and receiver angles.

The signal in units of contrast per radian of tilt is typically on the order of 1/radian or $10^{-6}$/µradian. This can also be derived from equation A-2 by assuming a Lambertian reflector (i.e., b=constant), for which the contrast per radian of tilt ($\Delta P/\langle P \rangle/\Delta \theta_t$), reduces to $\tan \theta_{i,n}$, which also gives 1/ radian at 45° from the normal and 6/radian at 80° from the normal.

The above results thus indicate that the modulated light signal is substantially linearly dependent upon the tilt magnitude of the target surface.

FIG. 7 is a graph illustrating a comparison between the tilt—as measured by a vibration imaging system according to the invention—and velocity, measured using a conventional geophone, of a vibrating surface, e.g. for studying seismic (or seismic-acoustic) signals. The results are plotted as a function of frequency with the optical (vibration imager) data plotted as square dots in units of optical contrast (left axis) and the geophone data plotted as diamond-shaped dots in units of vertical velocity (right axis). The excellent shape agreement of the two data sets shows the correlation between these two types of measurements, and validates the approach of the present invention.

FIG. 8 is a graph illustrating the spectral response of a system according to the invention as used in biological setting, in which voltage-sensitive dyes may be used to produce spatial-temporal maps of electrical activity in biological systems, such as the heart, neurons, etc. In this case, in a wavelength range of about 450 nm to 900 nm, the photo sensitivity is between a Q.E. (quantum efficiency) of 50% and 100%, with 100% being an ideal response. Thus, a broad spectral response can be achieved. FIG. 9 is a graph illustrating the frequency response the same biological setting, and shows that a substantially flat frequency response is achieved for vibrations out to several kHz.

EMBODIMENTS OF THE INVENTION

FIG. 10 is a diagram showing the basic configuration of a complete system according to one embodiment of the invention. In this example, a target object of interest is a helicopter 200, which will undergo oscillations while in operation that may be of analytical interest, to determine sources of malfunctions or for normal operation analysis. A detector array is included in a camcorder 210 or other detecting apparatus, and communicates (by a network connection, a wireless channel, or the like) to a processor-based system 220 coupled to a display 230 and user input apparatus such as keyboard 240 (and/or mouse, trackball or other digital input devices, not separately shown).

A suitable detector array 300 is shown in FIG. 11, and in this embodiment may include a 16×16 photodiode array (PDA), thus including 256 elements, though larger or smaller arrays may also be used. As an alternative to photodiodes, the individual detectors may be CMOS devices or other opto-electronic devices as appropriate.

A lens 250 (see FIG. 10) focuses light 260 reflected from the target object (here, the helicopter) onto the photodiodes of the PDA, and the photodiodes convert the light into electric currents in a conventional manner. These currents are filtered and amplified using standard electronic techniques, as described in greater detail below, and the outputs from the photodiodes are then digitized and recorded (i.e. digitally stored) at some predetermined frame rate, e.g. at a sample rate of 1 kHz. Other frame rates may be used, and the frame rate may be altered when desired, including dynamically altered in real time based upon predetermined criteria and/or user input.

In general, in some embodiments of the invention the processor or processing module will be configured to generate processed outputs relating to the detected acoustic signals at predetermined regular time intervals, where the time intervals are larger than time intervals corresponding to the predetermined sample rate. For instance, a sample rate of 1 kHz and a processing interval of 1 second may be used, a sample rate of 1 GHz and a processing interval of 0.1 millisecond (for a moving target, with very fast circuitry in the processing module), etc. The predetermined sample rate may itself be variable for different applications.

Lens 250 may be a conventional zoom or telescopic lens, allowing the user to isolate or focus in on a particular region of interest in the target object or scene.

Detector logic configured to carry out the conversion, digitization, filtering and amplification as described herein may in this embodiment be included in the camcorder 210, or may constitute a logic module separate from the primary detection optics and electronics, e.g. a logic module coupled to an output of a videocamera and coupled to an input of the system 220, or integrated into the system 220.

In one embodiment, the photodiodes of the PDA are AC-coupled to the amplifiers of the detector array and the signals are filtered prior to digitization, so that only changes (deltas) detected at each pixel or element of the PDA are recorded or stored. Storing only the deltas can greatly increase the dynamic range sensitivity of the system.

If the scene or target is stationery, then no signal (except perhaps noise) will be recorded. If part of a scene is vibrating, then changes in signals from the corresponding photodiodes of the array (which correspond to pixels in the resulting image) will be registered as fluctuations in the scene.

Those changes in the received signals will in general have associated frequencies and amplitudes due to the vibrations of regions in the scene corresponding to the respective photodiodes (or pixels). Thus, an apparatus according to FIG. 10 (with a detector array 300) is configured to spatially map the amplitudes and frequencies of vibrations on, e.g., the surface of an aircraft such as the helicopter 200. Collecting data from all pixels simultaneously or substantially simultaneously allows detection and analysis of spatial and phase relationships of the vibration over the entire target scene. ("Substantially simultaneous" data collection may be defined as data collection for different pixels within a time interval that results in correlation errors for the data for the different pixels no larger than some acceptable or predetermined limit.) The number of pixels or target spots can readily be expanded.

The interrogated area of the surface (including the "unit" area corresponding to a single pixel and the total imaged area) depends on the geometry of the scene or surface and the nature and setting of the lens in front of the sensor head, which may be a commercial off-the-shelf (COTS) lens. By using a standard zoom lens, the area of interest and the pixel size on the surface may be changed easily and dynamically. In an embodiment with a 16×16 photodiode (pixel) array in the sensor head, the interrogated area is divided into 256 subregions, as shown in FIG. 11, all of which are independently and simultaneously monitored for frequency and amplitude of tilt.

In one embodiment of an actual implementation of the present invention, the sensitivity of the vibration imager, in terms of tilt angle, has been determined to be about 1 µradian (0.00017°), which is approximately the angle subtended by a 1-meter high stick viewed from a distance of 1000 km. To support such a fine resolution, the dynamic range of the sensor is preferably about 24 dB, which can be achieved by:

(a) employing photodiodes with excellent inherent dynamic range;

(b) AC coupling to eliminate the large DC component due to the ambient light level;

(c) digitizing the resulting AC signal with high precision, e.g. 16-bit precision or greater; and/or (d) coherently integrating the signal over time (currently over about 1-second intervals).

The modulated-to-ambient light ratio (i.e., the contrast sensitivity) for this actual embodiment, which is of interest here, was on the order of $10^{-5}$ to $10^{-6}$. A contrast sensitivity of at least about $10^{-4}$ (and ideally, $10^{-5}$, $10^{6-}$or better) is desirable in ambient-light settings for usually expected vibrational amplitudes, for which the modulation of the incipient light due to the vibrations may be on the order of only a few ten-thousandths of a percent (roughly 0.0001% to 0.001%).

The helicopter 200 shown in FIGS. 10 and 11–14 is hovering, so that over at least short time intervals (e.g. a second or a few seconds), data may be taken without the helicopter changing position. With faster data collection, data may be taken of a moving object, with multiple data sets taken over a period of time short enough so that the target object has not appreciably moved. In either case, the detection of the desired data is carried out in real time, i.e. as an object undergoes vibration and with processing of the signals to generate an array of data correlated with imaged regions of the target scene.

If a root-mean-square (RMS) light modulation signal is calculated for each pixel's data, and the resulting values are visually superimposed on an image of the target object, where the RMS values are correlated spatially with the correct spots in the target object, an image such as that shown in FIG. 12 results, where the lighter pixels indicate a greater amount of vibration. As expected, the lightest regions are those near the helicopter blades and regions below the helicopter that are affected by the blades' rotation. Thus, FIG. 12 demonstrates that both visually and analytically a full-scene image is generated that includes useful information for analyzing the target scene.

FIG. 13 illustrates the same data as FIG. 12, with the underlaid image of the helicopter removed.

FIG. 14 illustrates an overlay (which may be an actual display overlay and/or may represent a correlation of data between the target scene and the data) of optical temporal frequency spectra with their correlated target spots (or pixels) in the target scene. The spectrum from each individual pixel, such as pixel 305, may be separately filtered, processed, stored and analyzed.

Thus, FIG. 15 is a graph representing information correlated with pixel 305. In this figure, the dashed-line graph represents data detected as optical sensor power spectral density (PSD) from an apparatus according to the invention, while the solid-line graph represents data detected as accelerometer displacement PSD from an accelerometer placed inside the helicopter. PSD represents the frequency response of a random or periodic signal, and indicates where the average power is distributed as a function of frequency.

In both the optical sensor PSD and the accelerometer PSD graphs, a strong 23 Hz signal (with multiples or harmonics thereof) is detected.

FIGS. 16 illustrates a scene of a nuclear power plant (in this example, Diablo Canyon near San Luis Obispo, Calif.). In this example, a system according to the invention is focused on the target scene, which includes among other regions a roof region 310 of the power plant. The RMS light modulation (or spectrum) for the entire target scene is illustrated in FIG. 17, while FIG. 18 shows a graph of the PSD for pixel 320 of FIG. 17. Similar to FIG. 15, FIG. 18 shows both the optical sensor PSD (dashed line) and an accelerometer PSD (solid line) from an accelerometer placed at the target region.

FIG. 18 demonstrates a peak at about 30 Hz (indicated by numeral 330), which may be attributed to generators within the building. Thus, the time-series recording of the data and generation of RMS spectra associated with individual target spots provides specific information useful for fault detection, analysis, etc. FIG. 19 illustrates a display of the optical power at 30 Hz for the array of pixels shown in FIG. 17. Optical power for other frequencies of interest may also be displayed. Note that the lighter regions of FIG. 19, which are correlated with the detected 30 Hz signal, correspond generally to the lighter regions of FIG. 17, which are correlated generally with regions in the target scene for which vibrations are detected.

HARDWARE FEATURES OF EMBODIMENTS OF THE INVENTION

FIG. 20 is a block diagram of a generalized circuit that may be used to implement the present invention. An optical filter 410 may be placed in front of the detector array or module 420 (which, as indicated above, may be incorporated into or coupled to a conventional camcorder, camera, or the like) to reduce reception at the detector module of undesired frequencies of light. The detector module 420 includes a detector array as described above, and its output is subject to analog processing, such as by being passed through a filter circuit 440 (discussed below), and thereafter digitized by a conventional analog-to-digital converter 450. A digital recorder 460 stores the digitized signals, and they are provided to a processor 470 for further processing and analysis.

FIG. 21 is a schematic diagram of a circuit suitable for incorporation into filter circuit 440 of FIG. 20. In this embodiment, a sensor head such as that available from Hamamatsu K.K. (headquartered in Hamamatsu City, Japan—see http://www.hamamatsu.com) with a suitable photodiode array may be used. A single photodiode channel 500 of a Hamamatsu sensor currently in use is shown in FIG. 21.

In this case, a high-pass filter 505 is used to increase the dynamic range of the frequency range of interest. An amplifier/filter board 510 includes both an AC-coupled channel and a DC-coupled channel for each pixel, i.e. for 256 channels in the embodiment discussed above. By filtering out the ambient light signal—which appears in the channels as DC (nonoscillating) signals—prior to digitizing it, the AC signals due to vibrations of the target scene can be effectively isolated and the dynamic range improved. Thus, the circuitry of the amplifier board 510 filters the signals output from the sensor head to separate the AC components of the signals from the DC components, and these components are then amplified and digitized. Each amplified photodiode AC output is independently digitized and passed to the computer or other processor-based system for storage and processing.

FIG. 22 illustrates an alternative circuit 520 for filtering out the DC component to isolate the AC signal. In this embodiment, a DC restoration is performed within the first stage transimpedance amplifier coupled to the photodiode. Circuit 520 is effectively a combination of high-pass filter 505 and circuit 500. In one embodiment, circuit 520 replaces both circuit 500 and the circuitry on the board 510, though its output 530 is passed through a second-stage amplifier (similar to the DC-coupled channel of board 510) before being input to the system 470.

One embodiment of AC coupling according to the invention is illustrated in FIGS. 23A–23C. FIG. 23A depicts the overall signal for a given pixel, showing a small AC oscillation riding on a large DC offset. In FIG. 23B, the DC portion of the signal has been substantially removed by the use of AC coupling (i.e. high-pass filtering), thus effectively isolating the AC component of the signal, which is then amplified. In FIG. 23C, the shown in FIG. 23B has been subjected to Fourier transform—e.g. FFT (fast Fourier transform) for real-time processing—or other frequency analysis, revealing the spectral content of the modulate signal. For the signal in this example, a resonant frequency response of about 87 Hz is visible in the resulting graph.

The simultaneous capture of acoustic signals across the detector array focused on the target region provides the flexibility of determining the nature of the acoustic phenomena giving rise to those signals, and in addition the channel-by-channel treatment and analysis of those signals, as described below. This detection and signal processing on the basis of individual pixels relating to target "unit" spots provides a powerful analytical tool.

Analysis of Oscillating and Transient Signals

FIGS. 24–31 illustrate application of a system of the invention to the detection and analysis of signals relating to oscillating and transient signals.

Periodic Signals

FIG. 24 is an illustration of an impulsive source 600 which generates an acoustic oscillation generally 610, which includes multiple generally periodic wavefronts 620–640, etc., which propagate outwards from the source 600, e.g. at a velocity of approximately 300 m/s. In a detector apparatus according to the invention, a sensor array 650 receives reflected light from a region of interest, in this case covering a region in which three wavefronts 620–640 are at least partially represented. Surface distortions are caused in the target region by the acoustic wave, which result in tilts in the surface that modulate the reflected light, as discussed above. A vibration imaging system according to the invention provides two-dimensional spatial information of this tilt as a function of time, effectively projected onto the pixel array.

In the far-field (relatively distant from the point of impact), the surface wave achieves substantially steady-state propagation, such that the disturbance has a relatively uniform effective wavelength.

In this example, the successive wavefronts are separated by about three pixels each, and thus one wavelength may be regarded as the distance in the target region corresponding to three pixels. If, for instance, each pixel represents a one-square-meter area, then the wavelength in this example is three meters. If the waves are propagating with a velocity of 300 m/s, then the frequency of the oscillation is 300 m/s divided by 3 meters, or 100 sec$^{-1}$ (100 Hz).

This is illustrated in FIG. 25, where the spatial frequency of the detected signals is represented in a one-dimensional spatial Fourier transform in the direction of wave propagation, showing a peak at a frequency of about 0.3 pixel$^{-1}$, i.e. a wavelength of about 3 pixels.

When a temporal or time-domain Fourier transform is performed in the direction of propagation (e.g. the x-direction in FIG. 24), a peak will represent an effective period in seconds. FIG. 26 illustrates the result of such a Fourier transform in this example, and shows a peak at period of 0.01 seconds, i.e. a frequency of 100 Hz.

Transient Signals

FIG. 27 is a sequence of diagrams illustrating a transient wavefront 700 propagating outward in the x-direction, superimposed on a detector array 710 which is used to detect reflected light from a target region subjected to a shock wave or the like resulting in formation of the wavefront 700. "Transient" is used here to indicate a disturbance that does not have a readily discernable or substantially uniform period or oscillation. In this case, the circuitry and processing logic associated with the detector array detects a signal traversing array pixels over time, as indicated by the graph of FIG. 28, wherein the slope of the pixels-vs.-time curve (or line) represents the velocity of the transient wavefront in pixels per second.

If a two-dimensional Fourier transform is carried out on the detected signals (after filtering, digitizing, etc. as discussed above), the resulting data or graph will show a correlation between the spatial frequency (here, 1/pixel in the direction of propagation) and the temporal frequency (here, 1/second or 1 Hz), assuming the same wavefront velocity (300 m/s) and target region area corresponding to each pixel (1 meter square) as in the example of FIGS. 24–26. Such a result is illustrated in FIG. 29, which depicts an ideal, uniform distribution of spatial and temporal frequencies. A diagonal correlation in temporal and spatial frequencies is evidence of the velocity of the signal. A two-dimensional Fourier transform can also be applied to the propagating wavefront example of FIGS. 24–26.

The data depicted in FIGS. 28 and 29 can be extrapolated into three dimensions (two spatial and one temporal), such that velocity vector across the array (with both x and y components) can be determined.

FIG. 30 illustrates the situation when a disturbance such as an atmospheric scintillation moves as a turbulent cell 800 across a target region of a vibration imaging array 810 according to the invention. This type of phenomenon may be analyzed according to the well-known "frozen flow" model. Although the cell 800 may be determined by some systems to be a source of noise (or random signals), a system according to the invention correctly determines that the cell is an optical disturbance moving in space (e.g. in the x-direction here) and time, similar to the transient wavefront example discussed above.

FIG. 31 is a plot of actual data generated by a system according to the invention, wherein a two-dimensional spatial-temporal Fourier transform has been performed on the data. The plot of FIG. 31 shows power density (as contours) vs. the spatial and temporal frequency. The presence of a path in the contours (marked by the diagonal line) indicates an effective velocity (in pixels/second), and is consistent with the frozen-flow model. If there were no spatial-temporal correlation, then the plot of FIG. 31 would simply show concentric circular contours about the origin, i.e. the zero spatial (1/pixel) and zero temporal (1/second) point.

Scintillations may be considered a noise source, particularly for the long-range sensing of vibrations. However, the ability to characterize and understand these sources leads to the ability to digitally or analytically filter such scintillations out of the data, and thus isolate other phenomena of interest.

INDUSTRIAL APPLICATIONS OF THE INVENTION

It will be appreciated from the above that apparatus according to the invention can be quickly and easily assembled, and detection of acoustic events in the target scene does not require contact or even proximity with the scene. Real-time acoustic imaging is achieved of multiple correlated points in the target scene, and the resulting acoustic signal data can be evaluated and post-processed in a nondestructive manner, allowing for different types of analysis at any time.

This leads to multiple types of applications for the invention, such as process monitoring on an assembly line (e.g. for vehicles, machinery, etc.), continuous health monitoring (pumps, bearings, flow monitoring, etc.), quality control (e.g. noise control), predictive/preventive maintenance by detecting incipient failure of machinery, and so on. Other applications include the use of an acoustic imaging apparatus according to the invention to detect seismic ground motion for oil exploration or to detect underground structures through the use of otherwise conventional seismic exploration techniques (e.g. by the use of explosions or other inducement of vibrations). Such underground structures may be naturally occurring—such as aquifers, oil deposits, ore deposits, etc.—or may be artificial, such as buried utilities, pipelines, land mines, or the like.

Example of potential applications in medical/forensic fields are also numerous. Vibration imaging according to the invention can be used for:

equantification of tremors or shaking due to Parkinson's disease or BET (benign essential tremor shaking) for drug development and clinical trials;

non-contact monitoring of a patient's vital signs, such as respiration, pulse, normal tremors (both rate and amplitude)—especially useful for burn victims;

neonatal monitoring, where patients are small relative to conventional monitoring "patches"; and detection of micro-expressions (eye motion, fidgeting, etc.) for non-contact lie detection of entire face or body.

These applications of the invention are all enabled by the full-image, non-contact nature of the invention, with its capability of pixel-by-pixel detection, processing and analysis. Other applications and advantages will be apparent based upon the foregoing disclosure.

The invention claimed is:

1. A system for detecting a light signal relating to the vibration of a target object, including:

an array of light amplitude modulation detectors, each detector in the array configured to receive a light signal from a corresponding region of the target object and to generate an output representing the received signal;

a plurality of filters, each filter configured to receive the output from one of the detectors and to generate from the received output at least one filtered signal relating to a vibration of the corresponding region of the target object; and a processing module configured to generate from each of the filtered light signals a processed output representing the vibration relating to the corresponding region.

2. The system of claim 1, wherein the light signal relates to an oscillation of the target object.

3. The system of claim 1, wherein the light signal relates to a transient pulse of the target object.

4. The system of claim 1, wherein at least a portion of the received signals include electromagnetic radiation reflected from the corresponding regions of the target object.

5. The system of claim 4, wherein the reflected radiation includes visible radiation.

6. The system of claim 4, wherein the reflected radiation includes infrared radiation.

7. The system of claim 4, wherein the reflected radiation includes ultraviolet radiation.

8. The system of claim 1, wherein at least a portion of the received signals include electromagnetic radiation emitted from the corresponding regions of the target object.

9. The system of claim 8, wherein the emitted radiation includes thermal IR radiation.

10. The system of claim 8, wherein the emitted radiation includes fluorescent radiation.

11. The system of claim 1, wherein the filters are configured to AC couple the outputs to generate filtered signals from which DC components have been at least partly removed.

12. The system of claim 1, wherein the processing module is configured to generate frequency information for each of the filtered signals.

13. The system of claim 12, wherein the processing module is configured to generate, for each filtered signal, a contrast signal representing a contrast attribute of the corresponding filtered signal.

14. The system of claim 13, wherein the processing module is configured to correlate the contrast attributes with the frequency information.

15. The system of claim 14, wherein the processing module is configured to generate an output representing a plot of contrast distribution across the array of detectors, the contrast distribution being associated with a given frequency.

16. The system of claim 1, wherein the detectors are configured to sample received signals at a predetermined rate.

17. The system of claim 16, wherein the predetermined rate is fixed.

18. The system of claim 16, wherein the predetermined rate is variable.

19. The system of claim 15, wherein the processing module is configured to generate the processed outputs at predetermined regular time intervals, the time intervals being of a length that is greater than a time interval corresponding to the predetermined sampling rate.

20. The system of claim 4, wherein at least a portion of the reflected signals are due to naturally occurring ambient electromagnetic radiation.

21. The system of claim 4, wherein at least a portion of the reflected signals are due to artificially generated electromagnetic radiation directed at the target object.

22. The system of claim 4, wherein the reflected electromagnetic radiation is at least in part from a collimated radiation source.

23. The system of claim 4, wherein the reflected electromagnetic radiation is at least in part from a coherent radiation source.

24. The system of claim 1, further including an apparatus configured to induce vibrations in the target object.

25. The system of claim 1, wherein the detectors comprise photodiodes.

26. The system of claim 1, wherein the detectors comprise CMOS detectors.

27. The system of claim 1, including an optical filter positioned between the array of the detectors and the target object.

28. The system of claim 1, wherein the processing module is configured to generate a contrast signal corresponding to the vibration of each corresponding region.

29. The system of claim 28, further including a visual output device coupled to the processing module and configured to generate a representation of the target object superimposed with the contrast signals correlated with their respective corresponding regions.

30. The system of claim 1, wherein the processing module is configured to generate a temporal spectral signal corresponding to the vibration of each corresponding region.

31. The system of claim 28, further including a visual output device coupled to the processing module and configured to generate a representation of the target object superimposed with the spectral signals correlated with their respective corresponding regions.

32. A method for detecting light signals relating to a vibratory target object, including the steps of:
  receiving a light signal from each of a plurality of regions of the target object at a corresponding plurality of light amplitude modulation detectors;
  generating from each received signal a signal that is correlated to a vibration of the corresponding region of the target object;
  digitizing each correlated signal;
  generating from the digitized signals an output representing the vibrations of the regions of the target object.

33. The method of claim 32, further including the step of executing a Fourier transform on the digitized signals.

34. The method of claim 32, wherein the plurality of detectors are arranged in a rectangular array.

35. The method of claim 32, wherein the light signals include modulated light reflected from the target object.

36. The method of claim 35, wherein the reflected light includes light having a frequency in at least one frequency range of visible, infrared and ultraviolet radiation.

37. The method of claim 32, wherein the light signals include modulated light emitted from the target object.

38. The method of claim 37, wherein the emitted light includes thermal infrared radiation.

39. The method of claim 37, wherein the emitted light includes fluorescent radiation.

40. The method of claim 32, further including the step of optically filtering the signals received from the plurality of regions.

41. The method of claim 32, further including the step of generating contrast signals from the received signals relating to the vibrations of the corresponding regions.

42. The method of claim 32, further including the step of displaying a representation of the target object visually correlated with the generated signals representing the vibrations of the corresponding regions.

43. The method of claim 32, wherein the generating step includes the step of generating a temporal spectral signal corresponding to the vibration of each corresponding region.

44. The method of claim 32, further including the step of extracting from the received signals a representation of an oscillation of the corresponding regions.

45. The method of claim 32, wherein the extracting step includes the step of AC-coupling the received signals.

46. The method of claim 45, wherein the extracting step includes the step of removing from the received signals at least one component representing ambient radiation in a vicinity of the target object.

47. A system for acoustically imaging a target object undergoing vibration, including:
  an array of photodetectors;
  a lens positioned to focus light signals received from individual regions of the target object onto the photodetectors, the light signals being modulated in a manner corresponding to vibrations of the individual regions;
  a circuit coupled to each photodetector configured to isolate vibration signals from the light signals;
  digitizing logic configured to digitize the vibration signals;

transform logic configured to extract frequency information from the digitized vibration signals; and imaging logic configured to correlate the extracted frequency information with the corresponding regions of the target object, the correlated frequency information representing an light image of the target region.

* * * * *